(12) United States Patent
Trembly

(10) Patent No.: US 9,271,789 B2
(45) Date of Patent: Mar. 1, 2016

(54) METHOD AND APPARATUS UTILIZING MAGNETIC NANOPARTICLES FOR STERILIZING FEMALE PLACENTAL MAMMALS, INCLUDING WOMEN

(71) Applicant: The Trustees of Dartmouth College, Hanover, NH (US)

(72) Inventor: B. Stuart Trembly, Hanover, NH (US)

(73) Assignee: The Trustees of Dartmouth College, Hanover, NH (US)

(*) Notice: Subject to any disclaimer, the term of this patent is extended or adjusted under 35 U.S.C. 154(b) by 235 days.

(21) Appl. No.: 13/945,610

(22) Filed: Jul. 18, 2013

(65) Prior Publication Data

US 2014/0020689 A1     Jan. 23, 2014

Related U.S. Application Data

(60) Provisional application No. 61/672,991, filed on Jul. 18, 2012.

(51) Int. Cl.
*A61B 18/04*     (2006.01)
*A61B 18/18*     (2006.01)
(Continued)

(52) U.S. Cl.
CPC . *A61B 18/18* (2013.01); *A61F 6/22* (2013.01); *A61F 6/225* (2013.01); *A61N 2/06* (2013.01); *A61B 2018/1861* (2013.01)

(58) Field of Classification Search
CPC ............. A61B 2018/00214; A61B 2018/0022; A61B 2018/00559; A61B 2017/4233; A61F 2007/0048; A61F 2007/005; A61F 2007/009; A61F 2007/0091; A61F 2007/0092; A61F 2007/126; A61F 7/12; A61F 7/123; A61N 2/02

See application file for complete search history.

(56) References Cited

U.S. PATENT DOCUMENTS 6,982,501 B1    1/2006   Kotha et al.
7,448,389 B1    11/2008   Kotha et al.
(Continued)

FOREIGN PATENT DOCUMENTS

WO     2009005656 A2     1/2009

OTHER PUBLICATIONS

PCT Application PCT/US2011/040722 International Search Report and Written Opinion dated Feb. 17, 2012, 10 pages.
(Continued)

*Primary Examiner* — Joseph Stoklosa
*Assistant Examiner* — Nicole L Pobre
(74) *Attorney, Agent, or Firm* — Lathrop & Gage LLP

(57) ABSTRACT

A method for local heating includes placing first magnetic material in a first lumen, and a second magnetic material in a second lumen from the first magnetic material to a magnetically permeable rod, then applying alternating magnetic fields. The first lumen may be a fallopian tube. A method of occluding fallopian tubes uses a catheter to inject first magnetic material into the tubes, injecting second magnetic fluid into uterus, introducing a magnetically-permeable rod into vagina, positioning a second end of the rod over the fallopian tube and applying an alternating magnetic field to the first magnetic material to heat it. The method is performed with apparatus having a coil wound over a magnetically-permeable rod, a high frequency AC generator coupled to the coil, a first magnetic fluid capable of generating heat in an alternating magnetic field, and a second magnetically-permeable magnetic fluid capable of conducting magnetic fields through a lumen.

9 Claims, 4 Drawing Sheets

(51) Int. Cl.
*A61F 6/22* (2006.01)
*A61N 2/06* (2006.01)

(56) References Cited

U.S. PATENT DOCUMENTS

| | | | |
|---|---|---|---|
| 8,688,229 | B2 | 4/2014 | Feucht et al. |
| 2006/0025713 | A1 | 2/2006 | Rosengart et al. |
| 2007/0088321 | A1 | 4/2007 | Quinn |
| 2011/0224479 | A1 | 9/2011 | Yager |
| 2013/0261368 | A1 | 10/2013 | Schwartz |
| 2013/0345670 | A1 | 12/2013 | Rajagopalan et al. |
| 2014/0149092 | A1 | 5/2014 | Nadobny et al. |

OTHER PUBLICATIONS

PCT Application PCT/US2015/040302 International Search Report and Written Opinion dated Oct. 13, 2015, 10 pages.

METHOD AND APPARATUS UTILIZING MAGNETIC NANOPARTICLES FOR STERILIZING FEMALE PLACENTAL MAMMALS, INCLUDING WOMEN

RELATED APPLICATION

The present application claims priority to U.S. Provisional Patent Application 61/672,991 filed 18 Jul. 2012, the contents of which are incorporated herein by reference.

The present application is related to the material of PCT/US2011/040722, the contents of which are incorporated herein by reference.

BACKGROUND

FIG. 1 and FIG. 2 are schematic sketches of the female reproductive system of many placental mammals. FIG. 1 illustrates the normal human and higher primate anatomy with simplex uterus, and FIG. 2 illustrates schematically the bicornuate or bipartite uterus as found in many other placental mammals including dogs, cats, and pigs, and which may occasionally be found as a birth defect in humans. Some other mammals, including rodents, may have two separate uteri, each with a separate cervix leading into their vagina.

The female reproductive system 100 of higher primates, or that of many other mammals 102, has a uterine body 104, 106, and a pair of fallopian tubes, including a right tube 108 and a left tube 110; in mammals having bicornuate or bipartite uteri the uterine body has a right 105 and left 107 uterine horn—normal pregnancies in these mammals often occur within the horns 105, 107. Each tube extends from the uterine body and ends in a multiplicity of fimbriae, the fimbriae being projections that surround an ovary, fimbriae 116 of the right tube surrounding a right ovary 112 and fimbriae 118 of the left tube surrounding a left ovary 114. When an oocyte is released by an ovary, the fimbriae 116, 118 capture the oocyte and direct that oocyte into a lumen, or passageway through, the associated fallopian tube 108, 110, and into the associated uterine horn or body. A cervix 120 demarcates a distal end of the uterus and separates the uterus 104, 106 from the vagina 122. (The vagina is not shown in FIG. 2.)

The vagina 122 has a passageway or lumen 124 extending from outside the body to the cervix, and the uterus has a passageway or lumen 126 extending from the cervix to each fallopian tube 108, 110. Each fallopian tube also has a lumen, the right tube having right fallopian lumen 128 and left tube having left fallopian lumen 130.

In order to prevent pregnancy, the fallopian tube lumens 128, 130, may be obstructed. A common surgical sterilization procedure involves cutting the tubes and tying them off, such that their lumen is no longer contiguous. In an earlier U.S. Pat. No. 6,485,486, the present inventor has suggested applying microwave energy to an antenna inserted into the fallopian tube lumen, the surrounding tissue being heated by the microwave energy and damaging a lining of the tube. In another application, PCT/US2011/040722, the present inventor has suggested heating a particle suspension located within the fallopian tube lumen to damage a lining of the tube sufficiently that the tube heals with scar tissue formation. In either method, the scar tissue blocks the tube, leaving the lumen no longer contiguous and preventing oocytes from reaching the uterus.

It is undesirable to obstruct the uterine lumen because this is the primary passageway for menstrual discharge.

SUMMARY

A method for occluding fallopian tubes includes using a catheter to inject a first magnetic material into the fallopian tube, injecting a second high-magnetic-permeability magnetic fluid into a lumen of the uterus, introducing a first end of a magnetically-permeable rod into the vagina, positioning a second end of the rod over the fallopian tube; and applying a high-frequency alternating magnetic field to the magnetic nanoparticle suspension in the fallopian tube, thereby heating the magnetic nanoparticle suspension. The method is performed with an apparatus having a magnetically-permeable rod, a coil wound around the rod, apparatus for providing a high frequency alternating current to the coil, a first magnetic fluid capable of generating heat in an alternating magnetic field, and a second magnetically-permeable magnetic fluid capable of conducting magnetic fields through a lumen of an organ.

DETAILED DESCRIPTION OF THE EMBODIMENTS

Figure 4:
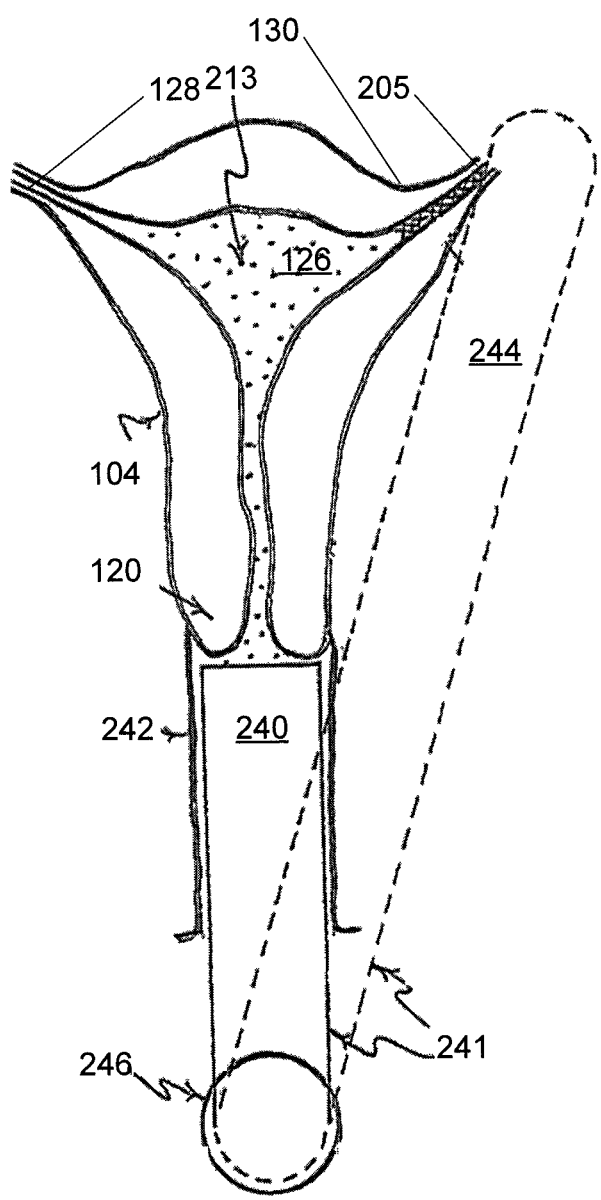
FIG. 4 is a top view cross-section schematically illustrating magnetic material placement in fallopian tubes and uterus, showing placement of the magnetically permeable rod.
Figure 5:
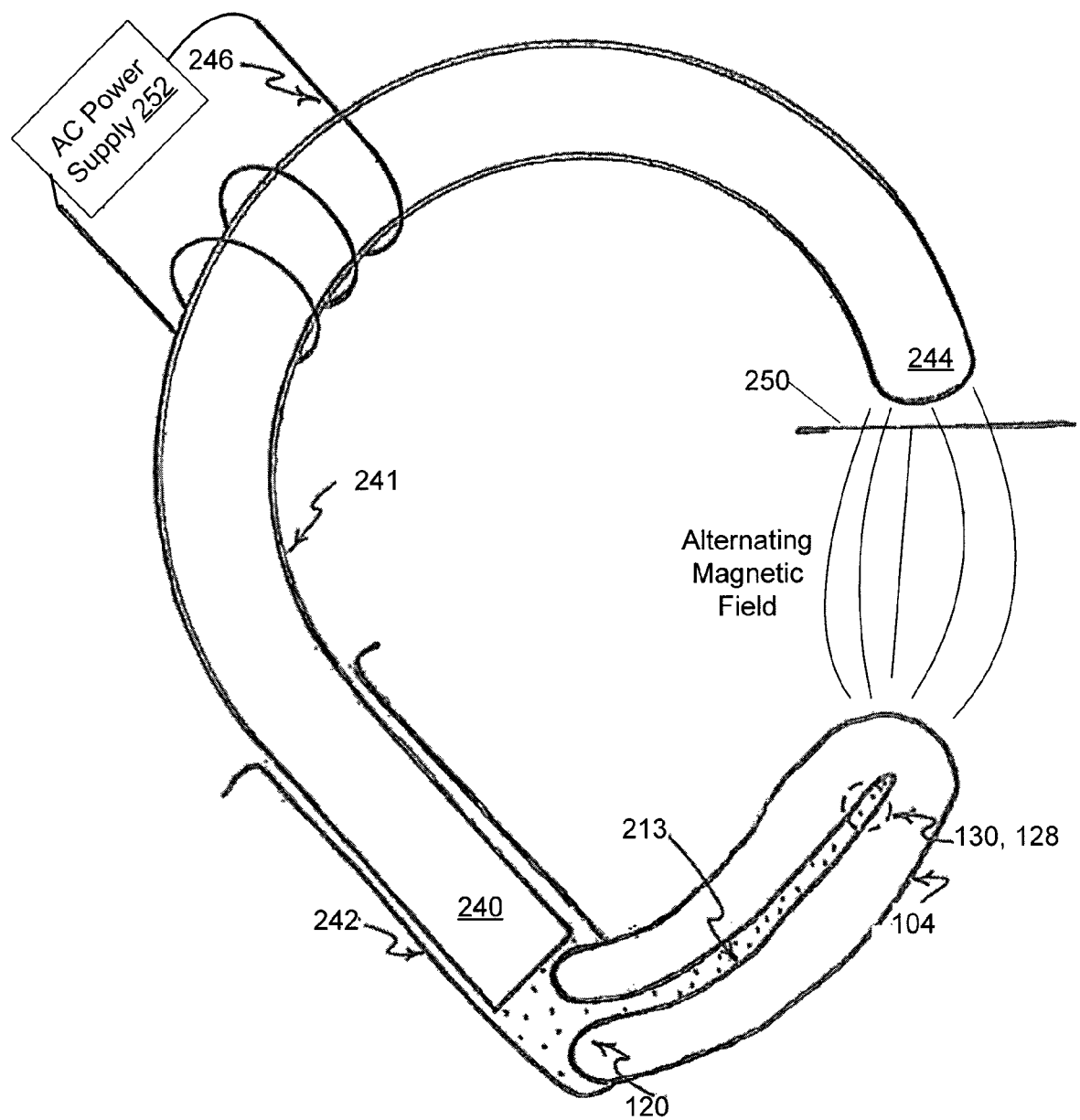
FIG. 5 is a lateral view cross-section schematically illustrating the uterus and positioning of the magnetically permeable rod and coil.

The procedure 200 (FIG. 3, with reference to FIGS. 4 and 5) to scar and occlude the fallopian tubes using magnetic nanoparticles for sterilizing female placental mammals, including women, begins with dilating 202 the cervix 120 of a subject. A catheter is then inserted 204 through the vagina, cervix, and uterus to a first fallopian tube. A magnetic nanoparticle suspension 205 is injected 206 into the first fallopian tube. The catheter is then repositioned 208 to a second fallopian tube, and magnetic nanoparticle suspension is injected 210 into the fallopian tube. The catheter is repositioned 212 into the uterus, the uterus of a subject being generally considered contiguous with an end of the fallopian tube, and a high-magnetic-permeability magnetic fluid 213 is injected 214 into the lumen of the uterus. The catheter is then withdrawn.

A magnetically-permeable rod has two ends. The first end 240 of the rod 241 is inserted 216 into the vagina 242. A second end 244 of the magnetically permeable rod is positioned over a first of the fallopian tubes to be heated. A high-frequency alternating current is then applied by an AC power supply 252 to energize 220 a coil 246 wound around the rod, causing a high-intensity, alternating, magnetic field to develop along the rod into the vagina, through the magnetically permeable fluid in the uterus, through the magnetic nanoparticle suspension in the fallopian tube, then through the abdominal wall 250 and abdominal tissue of the subject to the other end of the rod 244. The alternating magnetic field interacts with, and heats, the magnetic nanoparticle suspension 205 in the first fallopian tube to be heated.

The magnetically permeable rod is then repositioned 222 so the second end is over a second of the fallopian tubes to be heated, while the first end remains in the vagina. The high-frequency alternating current is then applied to energize 224 the coil again, heating the magnetic nanoparticle suspension in the second fallopian tube to be heated.

In this way, the materials of high magnetic permeability form a path, albeit incomplete, through which the magnetic field induced by the coil will pass preferentially; this path includes the Fallopian tube, which is to be heated therapeutically by the magnetic material enclosed within it.

It will be appreciated that an alternating current of smaller magnitude than required without the magnetically permeable rod will serve to produce a magnetic field of a desired magnitude in the Fallopian tube.

In a particular embodiment, the material of high permeability extending transvaginally to the cervix is a rod made of a material with low electrical conductivity, such as a ferrite material. The low electrical conductivity helps prevent heating of the material by eddy currents induced by the coil.

In a preferred embodiment, the material in the uterus is a biocompatible fluid containing particles of high permeability, which may be injected through the cervix without discomfort to the patient. This fluid fills the cervix to support the continuity of the preferred magnetic path from the coil outside the body to the Fallopian tube.

In another alternative embodiment, the biocompatible fluid containing particles of high permeability is contained within a balloon inserted transcervically into the uterus. This balloon is inflated under pressure, so as to increase the cross-sectional area of the preferred path for the magnetic field, and thus to reduce the leakage of the magnetic field lines into other, non-preferred paths.

In a particular embodiment, the material of high permeability is placed external to the body and encircled by the coil. In a particular embodiment, the material of high permeability has high resistivity to prevent heating by eddy currents.

In one embodiment, the magnetic material inserted into the Fallopian tube to be heated does not consist of magnetic particles suspended in a liquid, but is a solid magnetic material. In one preferred embodiment, the solid magnetic material is a flexible rod. In another preferred embodiment, the magnetic material is a helical coil, the rod or coil positioned through a catheter.

In another alternative embodiment, the material of high permeability inserted into the uterus is omitted, in order to simply the apparatus and method, however in this alternative embodiment higher power levels may be required at the coil in order to provide sufficient magnetic field density at the fallopian tube.

The magnetic nanoparticle suspension and high permeability magnetic fluid may then be flushed with saline solution through a catheter, or in an embodiment may be passed naturally, such as at a subsequent menstruation.

In an embodiment, the rod is a rigid rod having a hinge to permit positioning the second end 244 over the fallopian tube being treated. In an alternative embodiment, the rod is a flexible magnetically-permeable rod. In an embodiment, the rod is formed such that rotation of the rod in the vagina is sufficient to shift second end 244 from a position over one fallopian tube to a position over the other fallopian tube.

Figure 1:
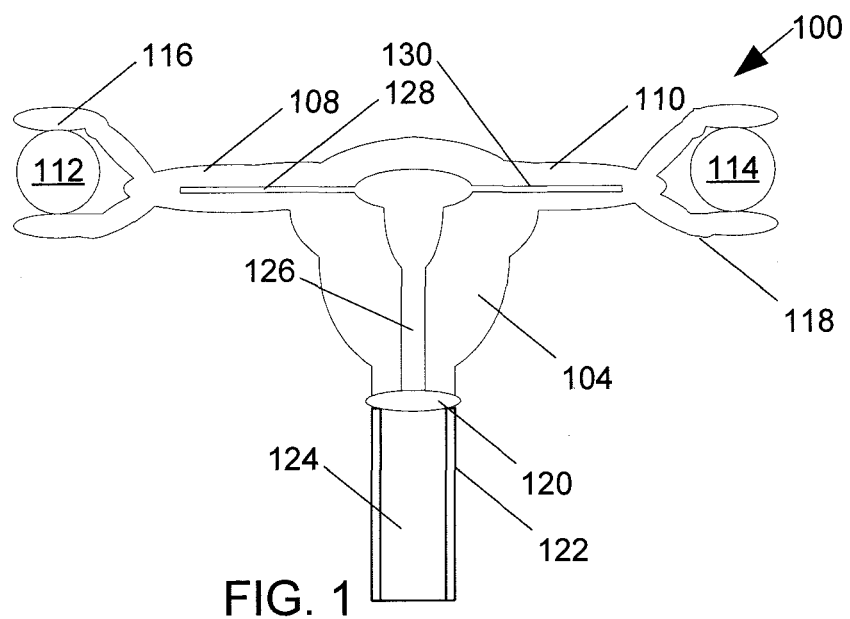
FIG. 1 is a schematic sketch of the female reproductive system with simplex uterus of most higher-primates and humans.
Figure 2:
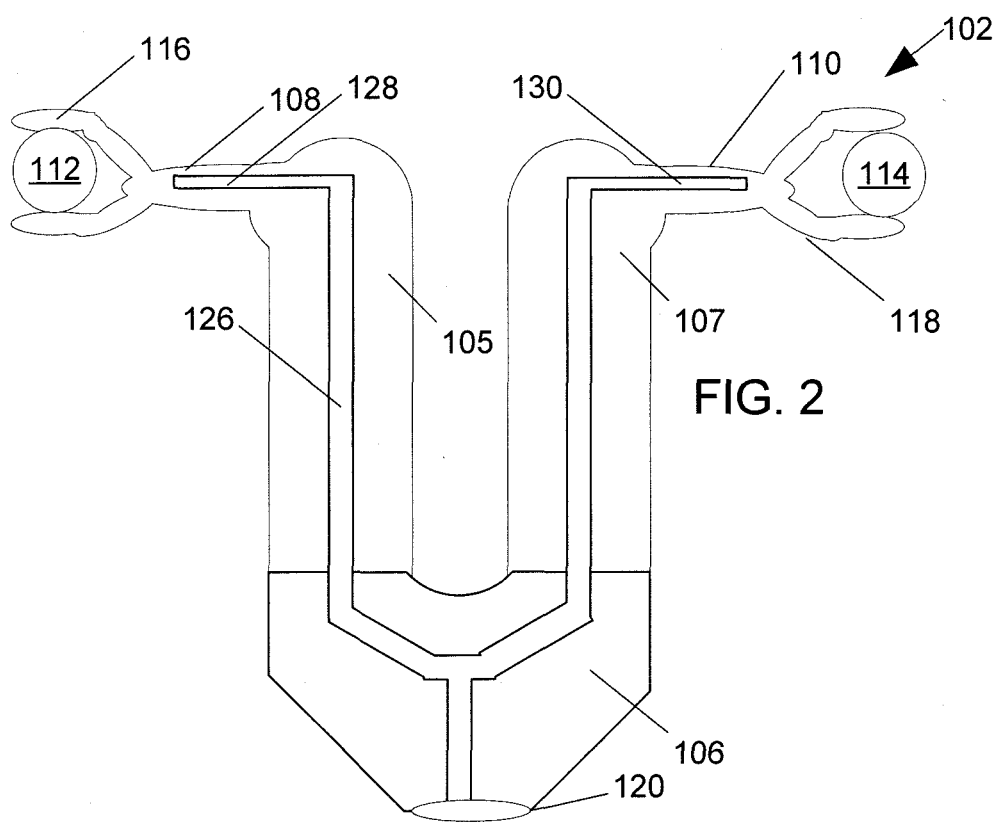
FIG. 2 is a schematic sketch of the female reproductive system with bicornuate or bipartite uterus as found in many mammals.
Figure 3:
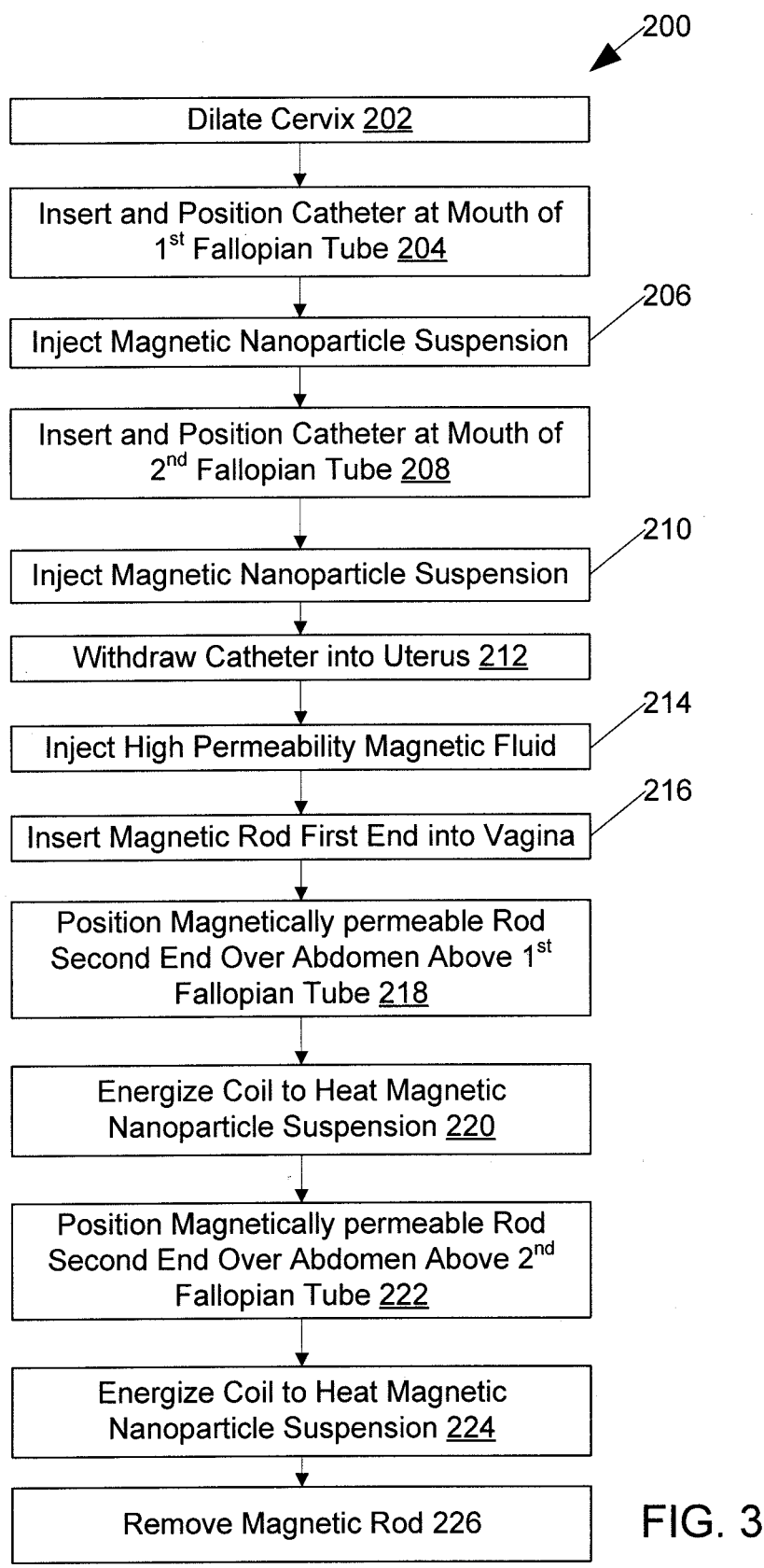
FIG. 3 is a flowchart of the method of scarring and obstructing the fallopian tubes.

While the procedure was described with reference to the simplex uterus of FIG. 3, it is equally applicable to the bicornuate or bipartite uteri of FIG. 2, or to the paired, separate, single-tube uteri of rodents.

When a subject has only one fallopian tube, such as in women where one tube has been removed due to an ectopic pregnancy, or when a single tube is to be treated such as for retreatment of a failed surgical sterilization, the steps of positioning the catheter at the second fallopian tube 208, the second injection of magnetic nanoparticle suspension 210, positioning the magnetically permeable rod over the second fallopian tube to be treated 222, and energizing the coil to heat the magnetic nanoparticle suspension 224 in the second fallopian tube are omitted.

In a particular embodiment, the magnetically permeable fluid in the uterus is Ferridex, which has a high permeability (forms a preferred path for magnetic field lines), but it has no pronounced heating ability. By contrast, in this embodiment the fluid in the fallopian tubes is a suspension of iron oxide nanoparticles of about 65 nanometer core diameter, where each iron oxide nanoparticle has a biocompatible coating, and the iron oxide nanoparticles are optimized for high energy absorption from alternating magnetic fields.

In yet another alternative embodiment, the magnetic material in the uterus fluid has a low particle density, and that in the fallopian tube a high particle density, in a fluid of otherwise identical composition. This difference in particle density gives rise to the required differential heating at the two sites. The reduced density of fluid in the uterus will produce a weaker preferred path of magnetic field lines through the uterus, but a preferential path still exists.

A similar method may be applied to other situations where it is desirable to apply heat within a first lumen of a fine or tortuous nonmagnetic tube or vessel, or within a lumen of a narrow passageway through nonmagnetic material, where the lumen is reachable through a second lumen of a larger diameter tube or passageway. In this method, the nanoparticle suspension is passed into the fine or tortuous tube, the magnetically permeable fluid in the larger diameter tube or passageway filling that passageway from a first end adjacent an entrance to the fine or tortuous tube to a second end, and a first end of the magnetically permeable rod placed adjacent to the second end of the larger diameter tube or passageway with a second end of the magnetically permeable rod placed as near as practical to the fine or tortuous tube. Then, a coil wound over the rod is energized with an alternating current to induce heating in the nanoparticle suspension.

Combinations of Features

The method and apparatus herein described has several elements that may be combined in various combinations. Among the combinations anticipated are the following combinations.

A method designated A for applying heat within a lumen of a first vessel includes: passing a magnetic nanoparticle suspension into the first vessel; placing a magnetically permeable fluid in a second lumen, the magnetically permeable fluid extending from an entrance to the first lumen to a second end of the second lumen; placing a first end of a magnetically permeable rod placed adjacent to the second end of the second lumen and a second end of the magnetically permeable rod as near as practical to the first lumen; and applying an alternating current to a coil wound over the magnetically permeable rod to induce heating in the nanoparticle suspension.

A method designated AA including the method designated A wherein the first and second lumens are passages of biological tissue.

A method designated AB including the method designated A or AA wherein the first lumen is a lumen of a fallopian tube, and the second lumen is a lumen of a uterus.

A method for occluding fallopian tubes designated B including inserting a catheter through a vagina, cervix, and uterus of a subject to a fallopian tube; injecting a first magnetic material into the fallopian tube; introducing a first end of a magnetically-permeable rod into the vagina (preferably with an end of the rod close to the uterus); positioning a second end of the magnetically permeable rod over the fallopian tube; applying a high-frequency alternating current to a coil wound around the rod, thereby forming and applying a high-intensity, alternating, magnetic field to the first magnetic material in the fallopian tube, and thereby heating the first magnetic material.

A method designated BA1 including the method designated B and further comprising injecting a second magnetic material into the uterus contiguous with the fallopian tube.

A method designated BA including the method designated B or BA1 wherein the first magnetic material includes magnetic nanoparticles suspended in a fluid.

A method designated BB including the method designated BA wherein the magnetic nanoparticles have a magnetic core of iron oxide covered with a biocompatible coating.

A method designated BC including the method designated BA or BB wherein the magnetic nanoparticles have a magnetic core of approximately 65 nanometers diameter.

A method designated BD including the method designated B, BA, BA1, BB, or BC wherein the second magnetic material is a high-magnetic-permeability material, and wherein the alternating magnetic field heats the first magnetic material to a higher temperature than the second magnetic material.

A method designated BE including the method designated B, BA, BA1, BB, BC, or BD wherein the step of heating the first magnetic material heats the first magnetic material to a temperature sufficient to cause scarring in the fallopian tube.

A method designated BF including the method designated B, BA, BA1, BB, BC, BD, or BF, further including injecting additional first magnetic material into a second fallopian tube, repositioning the second end of the rod over the second fallopian tube, applying a high-frequency alternating current to a coil wound around the rod, thereby forming and applying a high-intensity, alternating, magnetic field to the first magnetic material in the second fallopian tube, and thereby heating the first magnetic material sufficient to cause scarring in the second fallopian tube.

An apparatus designated C for occluding fallopian tubes includes a magnetically-permeable rod, a coil wound around the rod, apparatus for providing a high frequency alternating current to the coil, a first magnetic fluid capable of generating heat in an alternating magnetic field, and a second magnetically-permeable magnetic fluid.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A method for occluding fallopian tubes of a subject comprises:
    inserting a catheter through a vagina, cervix, and uterus of a subject to a fallopian tube;
    injecting a first magnetic material into the fallopian tube;
    introducing a first end of a magnetically-permeable rod into the vagina;
    positioning a second end of the magnetically permeable rod over the fallopian tube external to the subject;
    applying a high-frequency alternating current to a coil wound around the rod, thereby forming and applying a high-intensity, alternating, magnetic field to the first magnetic material in the fallopian tube, and thereby heating the first magnetic material.

2. The method of claim 1 further comprising injecting a second magnetic material into a uterus, the uterus contiguous with the fallopian tube.

3. The method of claim 2 wherein the first magnetic material comprises magnetic nanoparticles suspended in a fluid.

4. The method of claim 3 wherein the magnetic nanoparticles have a magnetic core of iron oxide covered with a biocompatible coating.

5. The method of claim 3 wherein the magnetic nanoparticles have a magnetic core of approximately 65 nanometers diameter.

6. The method of claim 2 wherein the second magnetic material is a high-magnetic-permeability material, and wherein the alternating magnetic field heats the first magnetic material to a higher temperature than the second magnetic material.

7. The method of claim 6 wherein the second magnetic material is contained within a balloon within the uterus.

8. The method of claim 6 wherein the step of heating the first magnetic material heats the first magnetic material to a temperature sufficient to cause scarring in the fallopian tube.

9. The method of claim 6 further comprising injecting additional first magnetic material into a second fallopian tube, repositioning the second end of the rod over the second fallopian tube, applying a high-frequency alternating current to a coil wound around the rod, thereby forming and applying a high-intensity, alternating, magnetic field to the first magnetic material in the second fallopian tube, and thereby heating the first magnetic material sufficient to cause scarring in the second fallopian tube.

* * * * *